United States Patent
Karl et al.

(10) Patent No.: US 9,150,685 B2
(45) Date of Patent: Oct. 6, 2015

(54) DIGLYCIDYL ETHERS OF 2-PHENYL-1,3-PROPANEDIOL DERIVATIVES AND OLIGOMERS THEREOF AS CURABLE EPOXY RESINS

(71) Applicant: BASF SE, Ludwigshafen (DE)

(72) Inventors: Ulrich Karl, Gruenstadt (DE); Monika Charrak, Ludwigshafen (DE); Hans-Josef Thomas, Korschenbroich (DE); Nicolas Marion, Mannheim (DE)

(73) Assignee: BASF SE, Ludwigshafen (DE)

( * ) Notice: Subject to any disclaimer, the term of this patent is extended or adjusted under 35 U.S.C. 154(b) by 65 days.

(21) Appl. No.: 14/074,192

(22) Filed: Nov. 7, 2013

(65) Prior Publication Data

US 2014/0128503 A1    May 8, 2014

Related U.S. Application Data

(60) Provisional application No. 61/723,839, filed on Nov. 8, 2012.

(51) Int. Cl.

| | |
|---|---|
| *C08G 59/24* | (2006.01) |
| *C08G 59/28* | (2006.01) |
| *C08G 59/30* | (2006.01) |
| *C08G 59/32* | (2006.01) |
| *C08G 59/38* | (2006.01) |
| *C08G 59/50* | (2006.01) |
| *C08G 59/62* | (2006.01) |
| *C08L 63/00* | (2006.01) |
| *C09J 163/00* | (2006.01) |
| *C09D 163/00* | (2006.01) |
| *C07D 301/28* | (2006.01) |
| *C07D 303/24* | (2006.01) |
| *C07D 303/26* | (2006.01) |
| *C07D 303/27* | (2006.01) |
| *C07D 303/28* | (2006.01) |

(52) U.S. Cl.
CPC ............ *C08G 59/245* (2013.01); *C07D 303/28* (2013.01); *C09D 163/00* (2013.01); *C09J 163/00* (2013.01)

(58) Field of Classification Search
None
See application file for complete search history.

(56) References Cited

U.S. PATENT DOCUMENTS

| 4,458,063 | A | * | 7/1984 | Kanno et al. .................. 528/418 |
|---|---|---|---|---|
| 4,481,348 | A | * | 11/1984 | Gladfelter et al. ............ 528/103 |
| 4,948,700 | A | | 8/1990 | Maeda et al. |
| 2004/0147638 | A1 | | 7/2004 | Kim et al. |
| 2009/0264669 | A1 | | 10/2009 | Upshaw |
| 2011/0152492 | A1 | | 6/2011 | Rappoport et al. |
| 2011/0178239 | A1 | * | 7/2011 | Mijolovic et al. ............. 524/605 |
| 2012/0116048 | A1 | | 5/2012 | Evans et al. |
| 2012/0130040 | A1 | | 5/2012 | Rappoport et al. |
| 2012/0232297 | A1 | | 9/2012 | Upshaw |

FOREIGN PATENT DOCUMENTS

| WO | WO 2010/100122 A1 | 9/2010 |
|---|---|---|
| WO | WO 2012/089657 A2 | 7/2012 |
| WO | WO 2012/091701 A1 | 7/2012 |

OTHER PUBLICATIONS

International Search Report issued Jan. 15, 2014 in Corresponding PCT/EP2013/072758.
Extended European Search Report issued Mar. 28, 2013 in Patent Application No. 12191862.7.
John W. Muskopf, et al., "Epoxy resins", Ullmann's Encyclopedia of Industrial Chemistry, vol. A9: Dithiocarbamic Acid to Ethanol, 1987, pp. 547-563.

* cited by examiner

*Primary Examiner* — Michael J Feely
(74) *Attorney, Agent, or Firm* — Oblon, McClelland, Maier & Neustadt, L.L.P.

(57) ABSTRACT

Cured epoxy resins are widespread on account of their outstanding mechanical and chemical properties. It is common to use epoxy resins based on bisphenol A diglycidyl ether or bisphenol F diglycidyl ether, but for many sectors these are problematic because of their endocrine effect. The present invention relates to 2-phenyl-1,3-propanediol diglycidyl ether derivates and to curable epoxy resin compositions based thereon, as alternatives to the bisphenol A or bisphenol F diglycidyl ethers and to the epoxy resin compositions based thereon.

19 Claims, 1 Drawing Sheet

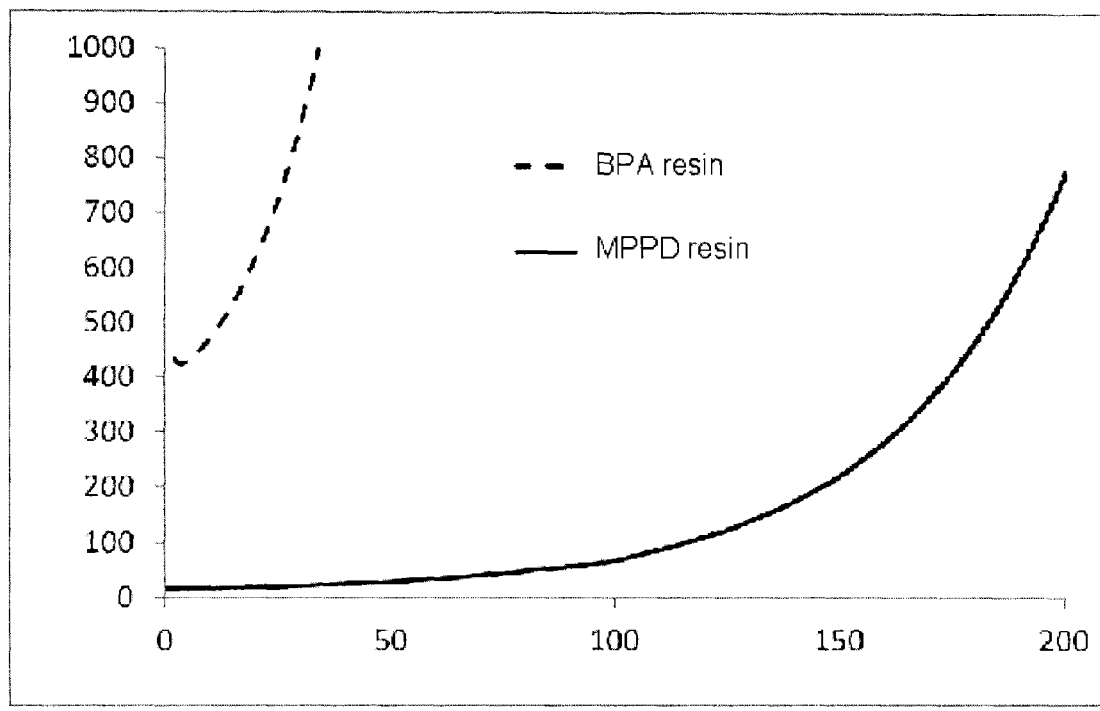

DIGLYCIDYL ETHERS OF 2-PHENYL-1,3-PROPANEDIOL DERIVATIVES AND OLIGOMERS THEREOF AS CURABLE EPOXY RESINS

The present invention relates to the 2-phenyl-1,3-propanediol diglycidyl ether derivatives, to processes for preparing them, and to the use thereof for producing adhesives, composite materials, moldings, or coatings. The present invention further relates to curable epoxy resin compositions comprising a curing component and a resin component which comprises at least one 2-phenyl-1,3-propanediol diglycidyl ether derivative or an oligomer based thereon as polyepoxide compound, and also to methods for curing these curable epoxy resin compositions and to epoxy resins that are obtainable or obtained by curing these curable epoxy resin compositions.

Epoxy resins is a designation customary for oligomeric compounds having on average more than one epoxide group per molecule, which are converted by reaction with suitable curing agents (hardeners) or by polymerization of the epoxide groups into thermosets, or cured epoxy resins. Cured epoxy resins, on account of their outstanding mechanical and chemical properties, such as high impact strength, high abrasion resistance, good heat and chemicals resistance, more particularly a high level of resistance toward alkalis, acids, oils and organic solvents, and high weathering resistance, excellent adhesiveness to a large number of materials, and high electrical insulation capacity, are widespread. They serve as a matrix for fiber composites and are often a major constituent in electrical laminates, structural adhesives, casting resins, coatings, and powder coating materials.

The majority of commercial (uncured) epoxy resins are prepared by coupling epichlorohydrin to compounds which possess at least two reactive hydrogen atoms, such as polyphenols, monoamines and diamines, aminophenols, heterocyclic imides and amides, aliphatic diols or polyols or dimeric fatty acids. Epoxy resins which derive from epichlorohydrin are referred to as glycidyl-based resins. Generally speaking, bisphenol A diglycidyl ether or bisphenol F diglycidyl ether, or the corresponding oligomers, are used as epoxy resins.

Exacting requirements are imposed especially on coatings of containers for the storage of foods and drinks. The coating accordingly is to resist strongly acidic or salty foods (e.g. tomatoes) or drinks, so that no corrosion occurs to the metal, which might in turn lead to contamination of the contents. Moreover, the coating must not impact the flavor or appearance of the foods. Since the production of the containers often involves further forming of containers that have already been coated, the coating must be flexible. Many contents, such as foods, are not pasteurized until they are in the can; the coating therefore, is required to withstand heating at 121° C. for at least 2 hours without damage and without migration of ingredients.

The use of epoxy resins based on bisphenol A or bisphenol F diglycidyl ethers is becoming identified as a problem in an increasing number of sectors, since the corresponding diols are seen as problematic on account of their endocrine effect.

To solve this problem, a variety of proposals have been made:

US 2012/0116048 discloses a bisphenol A (BPA) and bisphenol F (BPF) free polymer, which as well as ester bonds also comprises hydroxyether bridges, with use being made of diepoxides which are based on open-chain aliphatic diols such as neopentyl glycol (NPG), on simple cycloaliphatic diols such as 1,4-cyclohexanedimethanol or on aromatic diols such as resorcinol. From experience, however, the aliphatic and cycloaliphatic diols described produce coatings which are very soft and have low temperature and chemicals resistance.

WO 2012/089657 discloses a BPA-free preparation comprising a film-forming resin and an adhesion promoter. The resin is an epoxidized resin prepared for example from the diglycidyl ethers of NPG, ethylene glycol, propylene or dipropylene glycol, 1,4-butanediol or 1,6-hexanediol. Here, the same restrictions on the properties of the coating are anticipated as in the previous example.

US 2012/0130040 and US 2009/0264669 mention, inter alia, diglycidyl ethers of 2-phenyl-1,2-propanediol and the use thereof as a curable epoxide, without disclosing any details of the preparation of such a compound and of the curing thereof.

WO 2010/100122 proposes a coating system which is obtainable by reaction of an epoxidized vegetable oil with hydroxy-functional compounds such as, for example, propylene glycol, propane-1,3-diol, ethylene glycol, NPG, trimethylol propane, diethylene glycol, etc.

US 2004/0147638 describes a 2-layer (core/shell) system, wherein the core is formed from a BPA- or BPF-based epoxy resin, and the outer layer from, for example an acrylate resin. The critical issue here is whether the outer layer is truly able fully to prevent the migration of BPA or bisphenol A diglycidyl ether (BADGE) into the contents.

WO 2012/091701 proposes various diols and their diglycidyl ethers as a substitute for BPA or BADGE for epoxy resins, including derivatives of BPA and ring-hydrogenated BPA, alicyclic diols based on cyclobutane and diols having a furan ring as their parent structure.

The object on which the present invention is based is that of providing monomeric and/or oligomeric diglycidyl ether compounds for use in epoxy resin systems, especially as an at least partial substitute for BADGE in corresponding epoxy resin systems, particularly for use in the coating of containers.

The present invention relates accordingly to 2-phenyl-1,3-propanediol diglycidyl ether derivatives (PPD DGE derivatives) of the formula I

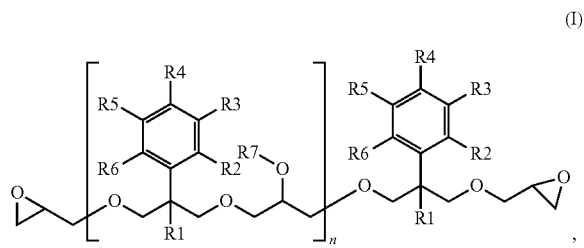

(I)

where
R1 is an alkyl group or an aryl group, preferably an alkyl group having 1 to 5 C atoms or an aryl group having 6 to 10 C atoms, more preferably a methyl group,
R2 to R6 independently of one another are each a hydrogen atom, an alkyl group having 1 to 4 C atoms, a halogen atom (F, Cl, Br, I), or a nitro group, preferably a hydrogen atom or an alkyl group having 1 to 4 C atoms,
R7 is a hydrogen atom or a glycidyl group, and
n is 0 to 100, preferably 0 to 30,
and where, furthermore, R2 and R3 or R3 and R4 may also together be a fused aromatic or heteroaromatic, thus resulting overall, for example, in a naphthyl or indolyl substituent.

In one particular embodiment, the present invention relates to 2-phenyl-1,3-propanediol diglycidyl ether derivatives (PPD DGE derivatives) of the formula I, where R1 is an alkyl group or an aryl group, preferably an alkyl group having 1 to 5 C atoms or an aryl group having 6 to 10 C atoms, more preferably a methyl group, R2 to R6 independently of one another are each a hydrogen atom, an alkyl group having 1 to 4 C atoms, a halogen atom (F, Cl, Br, I) or a nitro group, preferably a hydrogen atom or an alkyl group having 1 to 4 C atoms, R7 is a hydrogen atom or a glycidyl group, and n is 0 to 100, preferably 0 to 30.

In the case of PPD DGE derivatives of the formula I which have 2 or more R7 radicals (n=2 to 100), R7 in each case independently of any other is a hydrogen atom or a glycidyl group.

Alkyl groups for the purposes of the invention possess 1 to 20 C atoms. They may be linear, branched, or cyclic. They preferably have no substituents with heteroatoms. Heteroatoms are all atoms apart from C and H atoms.

Aryl groups for the purposes of the invention possess 6 to 20 C atoms. They preferably contain no substituents with heteroatoms. Heteroatoms are all atoms apart from C and H atoms.

One embodiment of the invention relates to oligomeric PPD DGE derivatives of the formula I where n is 1 to 100, preferably 1 to 30. An oligomeric PPD DGE derivative of the formula I for the purposes of the invention also includes a mixture of oligomeric PPD DGE derivatives having different ns and different substitution patterns for R7 (hydrogen atom or glycidyl group).

One embodiment of the invention relates to monomeric PPD DGE derivatives of the formula I with n=0.

One embodiment of the invention relates to mixtures of monomeric and oligomeric PPD DGE derivatives of the formula I.

One embodiment of the invention relates to the 2-phenyl-1,3-propanediol diglycidyl ether derivatives of the formula I, in which R1 is an alkyl group having 1 to 4 C atoms, preferably a methyl group, and R2 to R7 and n are as defined above. It relates more particularly to 2-phenyl-1,3-propanediol diglycidyl ether derivatives of the formula I, in which R1 is an alkyl group having 1 to 4 C atoms, preferably a methyl group, and R2 to R6 are each hydrogen atoms, n is 0 to 100, preferably 0 to 30, and R7 is as defined above (monomeric or oligomeric 2-alkyl-2-phenyl-1,3-propanediol diglycidyl ethers and monomeric or oligomeric 2-methyl-2-phenyl-1,3-propanediol diglycidyl ethers, respectively).

Preferred embodiments of the invention are monomeric 2-methyl-2-phenyl-1,3-propanediol diglycidyl ethers (MPPD DGE) corresponding to the formula I wherein R1 is a methyl group and R2 to R6 are each a hydrogen atom and n is 0, and also oligomeric MPPD DGE corresponding to the formula I wherein R1 is a methyl group and R2 to R6 are each a hydrogen atom, n is 1 to 100, preferably 1 to 30, and R7 is a hydrogen atom or a glycidyl group (independently of one another), and also mixtures of monomeric and oligomeric MPPD DGE.

The present invention further relates to a process for preparing PPD DGE derivatives of the formula I, comprising reacting the corresponding 2-phenyl-1,3-propanediol derivatives (PPD derivatives) of the formula II

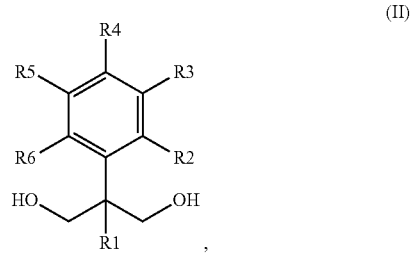

where
R1 to R6 have the same definition as for the PPD DGE derivatives of the formula I, with epichlorohydrin.

The reaction generally produces a mixture of monomeric and oligomeric PPD DGE derivative. The higher the excess of epichlorohydrin used, the greater the fraction of monomeric PPD DGE derivative. Monomeric PPD DGE derivatives can be separated from the oligomeric PPD DGE derivatives by means of separation techniques known to the skilled person, such as chromatographic, extractive or distillative methods, for example.

In one particular embodiment, 1 to 20 equivalents, preferably 2 to 10 equivalents, of epichlorohydrin are used for preparing the PPD DGE derivatives of the formula I. The reaction typically takes place in a temperature range from −10° C. to 120° C., preferably 20° C. to 60° C. To accelerate the reaction it is possible to add bases such as aqueous or alcoholic solutions or dispersions of inorganic salts, such as LiOH, NaOH, KOH, Ca(OH)$_2$ or Ba(OH)$_2$, for example. Furthermore, suitable catalysts such as tertiary amines can be used.

In another particular embodiment, the inventive conversion of the PPD derivatives of the formula II to the corresponding PPD DGE derivatives of the formula I is effected with 1 to 20 and preferably with 1 to 10 equivalents of epichlorohydrin at a temperature in a range from 20° C. to 180° C., preferably from 70° C. to 150° C., in the presence of a Lewis acid as a catalyst, preferably in the presence of tin(IV) chloride or boron trifluoride adducts such as boron trifluoride etherates. Subsequently, the reaction mixture is admixed with a base (for example dilute sodium hydroxide solution) and heated for a further period (for example 1 to 5 h) (for example under reflux). Thereafter, the product can be isolated by means of phase separation and washing steps with water.

The present invention further relates to processes for preparing PPD DGE derivative-based oligomers by reacting monomeric PPD DGE derivatives of the formula I with diols (chain extension). This is done by reacting monomeric PPD DGE derivative of the formula I (n=0) or a mixture of two or more PPD DGE derivatives of the formula I with different ns, where predominantly n is 0, with one or more diols. This mixture of two or more PPD DGE derivatives of the formula I preferably comprises the monomeric PPD DGE derivative (n=0) to an extent of at least 60 weight %. For this purpose it is preferred to use 0.01 to 0.95, more preferably 0.05 to 0.8, more particularly 0.1 to 0.4 equivalent of the diol, based on the PPD DGE derivative used. A substoichiometric amount of the diol or diols is preferably used to bring about an average of more than 1, preferably more than 1.5, more preferably more than 1.9 epoxide group(s) per molecule in the resultant PPD DGE derivative-based oligomer. The reaction takes place typically in a temperature range from 50° C. to 200° C., preferably 60° C. to 160° C. Suitable diols are customarily aromatic, cycloaliphatic or aliphatic dihydroxy compounds, examples being furandimethanol, ring-hydrogenated bisphenol A, ring-hydrogenated bisphenol F, neopentyl glycol, bisphenol A, bisphenol F or bisphenol S, preferably furandimethanol, ring-hydrogenated bisphenol A or ring-hydrogenated bisphenol F.

Accordingly, the present invention also provides PPD DGE derivative-based oligomers, which are obtainable or obtained by reacting a monomeric PPD DGE derivative of the formula I (n=0) or a mixture of two or more PPD DGE derivatives of the formula I with different ns, where predominantly n is 0, with one or more diols. This mixture of two or more PPD DGE derivatives of the formula I preferably comprises the monomeric PPD DGE derivative (n=0) to an extent of at least 60 weight %. In one particular embodiment, the one or more diols used are not identical with the PPD derivative of the formula II that corresponds to the PPD DGE derivatives of the formula I, and so, as a result, PPD DGE derivative-based co-oligomers are obtainable or obtained.

In one particular embodiment, the present invention relates to processes for preparing PPD DGE derivative-based oligomers starting from monomeric PPD DGE derivatives of the formula I, where the monomeric PPD DGE derivative of the formula I (n=0) or a mixture of two or more PPD DGE derivatives of the formula I with different ns, where predominantly n is 0, is reacted with the corresponding PPD derivative of the formula II. This mixture of two or more PPD DGE derivatives of the formula I preferably comprises the monomeric PPD DGE derivative (n=0) to an extent of at least 60 weight %. For this purpose, it is preferred to use 0.01 to 0.95, more particularly 0.1 to 0.4, equivalent of the PPD derivative of the formula II, based on the PPD DGE derivative of the formula I used. A substoichiometric amount of the PPD derivative of the formula II is preferably used to produce an average of more than 1, preferably more than 1.5, more preferably more than 1.9 epoxide groups per molecule in the resultant PPD DGE derivative-based oligomer. The reaction takes place typically in a temperature range from 50° C. to 200° C., preferably 60° C. to 160° C.

In an analogous way it is also possible to carry out specific preparation of higher molecular mass oligomeric PPD DGE derivatives of the formula I, starting from oligomeric PPD DGE derivatives of the formula I with a lower degree of oligomerization.

The present invention also relates to curable epoxy resin compositions comprising a curing component, which comprises at least one curing agent, and a resin component, which comprises at least one PPD DGE derivative-based polyepoxide compound selected from the group consisting of PPD DGE derivatives of the formula I (monomeric and/or oligomeric) and PPD DGE derivative based co-oligomer.

The present invention preferably relates to curable epoxy resin compositions comprising a curing component, which comprises at least one curing agent, and a resin component, which comprises at least one PPD DGE derivative-based polyepoxide compound selected from the group consisting of PPD DGE derivatives of the formula I (monomeric and/or oligomeric).

In one particular embodiment the present invention relates to curable epoxy resin compositions comprising a curing component, which comprises at least one curing agent, and a resin component, which comprises at least one oligomeric PPD DGE derivative of the formula I (n=1 to 100, preferably 1 to 30), the epoxide equivalent (EEW) of the oligomeric PPD DGE derivatives of the formula I used being on average between 130 and 3000 g/mol, more particularly between 140 and 1000 g/mol.

In one particular embodiment the curable epoxy resin composition of the invention contains less than 40 weight %, preferably less than 10 weight %, more preferably less than 5 weight %, very preferably less than 1 weight % of bisphenol A or F-based compounds, based on the overall resin component. The curable epoxy resin composition of the invention is preferably free from bisphenol A or F based compounds. Bisphenol A or F based compounds for the purposes of the present invention are bisphenol A and F themselves, their diglycidyl ethers, and also oligomers or polymers based thereon.

In one particular embodiment of the curable epoxy resin composition of the invention, the PPD DGE derivative-based polyepoxide compounds account in total for a fraction of at least 40 weight %, preferably at least 60 weight %, more particularly at least 80 weight %, based on the overall resin component.

The compounds of the formula I of the invention are also suitable for use as reactive diluents, especially as reactive diluents for BADGE-, bisphenol F diglycidyl ether-, tetraglycidylmethylenedianiline-, cresol-, novolac- or triglycidylaminophenol-based epoxy resins, since they are suitable for lowering the viscosity of other epoxy resins, especially BADGE-, bisphenol F diglycidyl ether-, tetraglycidylmethylenedianiline-, cresol-, novolac- or triglycidylaminophenol-based epoxy resins, in the resin component and in the curable composition. Advantageously, the addition of the compounds of the formula I of the invention as reactive diluents leads to a comparatively small reduction in the glass transition temperature.

Accordingly, the present invention, in a particular embodiment, relates to curable compositions comprising a curing component, which comprises at least one curing agent, and a resin component which comprises at least one PPD DGE derivative-based polyepoxide compound selected from the group consisting of PPD DGE derivatives of the formula I (monomer), and at least one epoxy resin selected from the group consisting of diglycidyl ethers of bisphenol A, diglycidyl ethers of bisphenol F (BFDGE), diglycidyl ethers of ring-hydrogenated bisphenol A, diglycidyl ethers of ring-hydrogenated bisphenol F, tetraglycidylmethylenedianiline, cresol epoxy resin, novolac epoxy resin and triglycidylaminophenols and oligomers thereof. In this case, the at least one PPD DGE derivative-based polyepoxide compound makes up a total proportion of preferably up to 30% by weight, more preferably up to 25% by weight, very preferably from 1 to 20% by weight, particularly from 2 to 20% by weight, very particularly from 5 to 15% by weight, based on the resin component (epoxy resin(s) and PPD DGE derivative-based polyepoxide compound(s)) of the curable composition.

Accordingly, the present invention also relates to a resin component comprising at least one PPD DGE derivative-based polyepoxide compound selected from the group consisting of PPD DGE derivatives of the formula I (monomer), and at least one epoxy resin selected from the group consisting of diglycidyl ethers of bisphenol A, diglycidyl ethers of bisphenol F (BFDGE), diglycidyl ethers of ring-hydrogenated bisphenol A, diglycidyl ethers of ring-hydrogenated bisphenol F, tetraglycidylmethylenedianiline, cresol epoxy resin, novolac epoxy resin and triglycidylaminophenols and oligomers thereof. In this case, the at least one PPD DGE derivative-based polyepoxide compound makes up a proportion of preferably up to 30% by weight, more preferably up to 25% by weight, very preferably from 1 to 20% by weight, particularly from 2 to 20% by weight, very particularly from 5 to 15% by weight, based on the resin component (epoxy resin(s) and PPD DGE derivative-based polyepoxide compound(s)) of the curable composition.

In one preferred embodiment of the curable epoxy resin composition of the invention, the overall resin component accounts for at least 10 weight %, more particularly at least 25 weight %, based on the overall curable epoxy resin composition.

For the purposes of the present invention all epoxide compounds and only the epoxide compounds, of the curable epoxy resin composition are to be assigned to the resin component. Epoxide compounds for the purposes of the present invention are compounds having at least one epoxide group—hence including, for example, corresponding reactive diluents.

The epoxide compounds of the resin component preferably contain on average at least 1.1, more preferably at least 1.5, more particularly at least 1.9 epoxide groups per molecule.

Curing agents for the purposes of the invention are compounds suitable for producing crosslinking of the PPD DGE derivative-based polyepoxide compounds of the invention.

Reaction with curing agents can be used to convert polyepoxide compounds into infusible, three-dimensionally "crosslinked", thermoset materials.

In the curing of epoxy resins, a distinction is made between two types of curing. In the first case, the curing agent has at least two functional groups which are able to react with the oxirane groups and/or hydroxyl groups of the polyepoxide compounds, with formation of covalent bonds (polyaddition reaction). In the course of curing, a polymeric network is then formed, made up of units which originate from the polyepoxide compounds and units originating from the curing agent molecules, these units being linked covalently to one another, and the degree of crosslinking being controllable via the relative amounts of the functional groups in the curing agent and in the polyepoxide compound. In the second case a compound is used which brings about the homopolymerization of polyepoxide compounds with one another. Such a compound is often also termed an initiator or catalyst. Homopolymerization inducing catalysts are Lewis bases (anionic homopolymerization; anionically curing catalysts) or Lewis acids (cationic homopolymerization; cationically curing catalysts). They bring about the formation of ether bridges between the epoxide compounds. It is assumed that the catalyst reacts with a first epoxide group, accompanied by ring opening, with formation of a reactive hydroxyl group, which reacts in turn with a further epoxide group with formation of an ether bridge, so leading to a new reactive hydroxyl group. On account of this reaction mechanism, the substoichiometric use of such catalysts is sufficient for curing. Imidazole is an example of a catalyst which induces the anionic homopolymerization of epoxide compounds. Boron trifluoride is an example of a catalyst which triggers a cationic homopolymerization. Additionally, mixtures of different curing agents which enter into a polyaddition reaction, and mixtures of curing agents which induce homopolymerization, and also mixtures of curing agents which undergo polyaddition reaction and curing agents which induce homopolymerization, can be used for the curing of polyepoxide compounds.

Suitable functional groups which are able to enter into a polyaddition reaction with the oxirane groups of polyepoxide compounds (epoxy resins) are, for example, amino groups, hydroxyl groups, thioalcohols and derivatives thereof, isocyanates, and carboxyl groups and/or derivatives thereof, such as anhydrides. Accordingly, curing agents used for epoxy resins typically include aliphatic, cycloaliphatic and aromatic polyamines, carboxylic anhydrides, polyamidoamines, amino resins such as, for example, formaldehyde condensation products of melamine, urea, benzoguanamine or phenolic resins such as novolaks, for example. Oligomeric or polymeric, acrylate-based curing agents with hydroxy functions or glycidyl functions in the side chain, and also epoxyvinyl ester resins, are also used. The skilled person is aware of those applications for which a fast- or slow-acting curing agent is used. For example, for storage-stable one-component formulations, he or she will use a curing agent which is very slow-acting (or which acts only at a relatively high temperature). Optionally, a curing agent will be used which is liberated as an active form only under application conditions, examples being ketimines or aldimines. Known curing agents possess a linear or no more than slightly crosslinked structure. They are described, for example in Ullmann's Encyclopedia of Industrial Chemistry, 5th edition on CD-ROM, 1997, Wiley-VCH, chapter "Epoxy Resins", hereby incorporated in full by reference.

Examples of suitable curing agents for the curable epoxy resin composition of the invention include polyphenols, polycarboxylic acids, polymercaptans, polyamines, primary monoamines, sulfonamides, aminophenols, aminocarboxylic acids, carboxylic anhydrides, carboxylic acids containing phenolic hydroxyl groups, sulfanilamides, and also mixtures thereof. In the context of this invention, the respective poly compounds (e.g. polyamine) also include the corresponding di compounds (e.g. diamine).

Preferred curing agents for the curable epoxy resin composition of the invention are amino hardeners and phenolic resins.

In one particular embodiment the curable epoxy resin composition of the invention comprises an amino hardener as curing agent. Amino hardeners suitable for the polyaddition reaction are compounds which possess at least two secondary or at least one primary amino group(s). The linking of the amino groups of the amino hardener with the epoxide groups of the polyepoxide compound forms polymers whose units originate from the amino hardeners and from the polyepoxide compounds. Amino hardeners are therefore used generally in a stoichiometric ratio to the epoxide compounds. If, for example, the amino hardener has two primary amino groups, and can therefore be coupled with up to four epoxide groups, crosslinked structures may be formed.

The amino hardeners of the curable epoxy resin composition of the invention possess at least one primary amino group or two secondary amino groups. Starting from polyepoxide compounds having at least two epoxide groups, curing can be accomplished by a polyaddition reaction (chain extension) using an amino compound having at least two amino functions. The functionality of an amino compound here corresponds to its number of NH bonds. A primary amino group therefore has a functionality of 2, while a secondary amino group has a functionality of 1. The linking of the amino groups of the amino hardener with the epoxide groups of the polyepoxide compound produces polymers from the amino hardener and the polyepoxide compound, the epoxide groups being reacted to form free OH groups. It is preferred to use amino hardeners having a functionality of at least 3 (for example, at least 3 secondary amino groups or at least one primary and one secondary amino group), more particularly those having two primary amino groups (functionality of 4).

Preferred amino hardeners are Dimethyl Dicykan (DMDC), dicyandiamide (DICY), isophoronediamine (IPDA), diethylenetriamine (DETA), triethylenetetramine (TETA), bis(p-aminocyclohexyl)methane (PACM), methylenedianiline (e.g. 4,4'-methylenedianiline), polyetheramines, e.g. polyetheramine D230, diaminodiphenylmethane (DDM), diaminodiphenylsulfone (DDS), 2,4-toluenediamine, 2,6-toluenediamine, 2,4-diamino-1-methylcyclohexane, 2,6-diamino-1-methylcyclohexane, 2,4-diamino-3,5-diethyltoluene, 2,6-diamino-3,5-diethyltoluene, 1,2-diaminobenzene, 1,3-diaminobenzene, 1,4-diaminobenzene, diaminodiphenyl oxide, 3,3',5,5'-tetramethyl-4,4'-diaminobiphenyl and 3,3'-dimethyl-4,4'-diaminodiphenyl, and also aminoplast resins such as, for example, condensation products of aldehydes such as formaldehyde, acetaldehyde, crotonaldehyde or benzaldehyde with melamine, urea or benzoguanamine, and also mixtures thereof. Particularly preferred amino hardeners for the curable composition of the invention are Dimethyl Dicykan (DMDC), dicyandiamide (DICY), isophoronediamine (IPDA) and methylenedianiline (e.g. 4,4'-methylenedianiline) and also aminoplast resins such as, for example, condensation products of aldehydes such as formaldehyde, acetaldehyde, crotonaldehyde or benzaldehyde with melamine, urea or benzoguanamine.

In the context of the curable epoxy resin composition of the invention, polyepoxide compound and amino hardener are preferably used in an approximately stoichiometric ratio in terms of the epoxide and amino functionalities. Particularly suitable ratios of epoxide groups to amino functionality are 1:0.8 to 0.8:1.

In one particular embodiment the curable epoxy resin composition of the invention comprises a phenolic resin as curing agent. Phenolic resins suitable for the polyaddition reaction possess at least two hydroxyl groups. Linking of the hydroxyl groups of the phenolic resin with the epoxide groups of the polyepoxide compound forms polymers whose units originate from phenolic resins and from the polyepoxide compounds. Phenolic resins can generally be used both in a stoichiometric ratio and in a substoichiometric ratio to the epoxide compounds. When substoichiometric amounts of the phenolic resin are used the reaction of the secondary hydroxyl groups of the existing epoxy resin with epoxide groups is promoted by the use of suitable catalysts.

Examples of suitable phenolic resins are novolaks, phenolic resoles, condensation products of aldehydes (preferably formaldehyde and acetaldehyde) with phenols in general. Preferred phenols are phenol, cresol, xylenols, p-phenylphenol, p-tert-butylphenol, p-tert-amylphenol, cyclopentylphenol, and p-nonyl- and p-octylphenol.

The curable epoxy resin composition of the invention may also comprise an accelerator for the curing. Suitable curing accelerators are, for example, imidazole or imidazole derivatives or urea derivatives (urons), such as, for example, 1,1-dimethyl-3-phenylurea (fenuron). The use of tertiary amines such as, for example, triethanolamine, benzyldimethylamine, 2,4,6-tris(dimethylaminomethyl)phenol and tetramethylguanidine as curing accelerators has also been described (U.S. Pat. No. 4,948,700). It is known, for example, that the curing of epoxy resins with DICY can be accelerated by addition of fenuron.

The curable epoxy resin composition of the invention may also comprise a diluent.

Diluents for the purposes of this invention are conventional diluents or reactive diluents. The addition of diluent to a curable epoxy resin composition typically lowers its viscosity.

Conventional diluents are, customarily, organic solvents or mixtures thereof, examples being ketones such as acetone, methyl ethyl ketone, methyl isobutyl ketone (MIBK), diethyl ketone or cyclohexanone, esters of aliphatic carboxylic acids such as ethyl acetate, propyl acetate, methoxypropyl acetate or butyl acetate, glycols such as ethylene glycol, diethylene glycol, triethylene glycol or propylene glycol etc., glycol derivatives such as ethoxyethanol, ethoxyethanol acetate, ethylene or propylene glycol monomethyl or dimethyl ethers, aromatic hydrocarbons such as toluene or xylenes, aliphatic hydrocarbons such as heptane, for example, and also alkanols such as methanol, ethanol, n- or isopropanol or butanols. In the course of the curing of the epoxy resin, they evaporate from the resin composition. This can lead to an unwanted reduction in resin volume (contraction) or to the formation of pores, and so may adversely affect mechanical properties of the cured material such as, for example, the fracture resistance, or even the surface properties.

Reactive diluents are substances of low molecular mass which, in contrast to conventional solvents, have functional groups, generally oxirane groups, which are able to react with the hydroxyl groups of the resin and/or with the functional groups of the curing agent, with formation of covalent bonds. Reactive diluents in the sense of the present invention are aliphatic or cycloaliphatic compounds. They do not evaporate in the course of curing, but instead are bound covalently, in the course of curing, into the resin matrix as it forms. Examples of suitable reactive diluents are mono- or polyfunctional oxiranes. Examples of monofunctional reactive diluents are glycidyl ethers of aliphatic and cycloaliphatic monohydroxy compounds having in general 2 to 20 C atoms such as, for example, ethylhexyl glycidyl ether and also glycidyl esters of aliphatic or cycloaliphatic monocarboxylic acids having generally 2 to 20 C atoms. Examples of polyfunctional reactive diluents are, in particular, glycidyl ethers of polyfunctional alcohols having in general 2 to 20 C atoms, and containing on average typically 1.5 to 4 glycidyl groups, such as 1,4-butanediol diglycidyl ether, 1,6-hexanediol diglycidyl ether, diethylene glycol diglycidyl ether or the glycidyl ethers of trimethylolpropane or of pentaerythritol. Reactive diluents described to date do enhance the viscosity properties of the epoxy resin compositions, but in many cases they impair the hardness of the cured resin and result in a relatively low solvent resistance. It is also known that the reactive diluents lower the reactivity of the epoxy resin compositions formulated with them, resulting in longer cure times.

The curable epoxy resin composition of the invention may also include fillers, such as pigments. Suitable fillers are metal oxides such as titanium dioxide, zinc oxide and iron oxide, or hydroxides, sulfates, carbonates, and silicates of these or other metals, examples being calcium carbonate, aluminum oxide, and aluminum silicates. Further suitable fillers are, for example, silicon dioxide, fumed or precipitated silica, and also carbon black, talc, barite or other non-toxic pigments. Mixtures of the fillers can be used as well. The weight fraction of the fillers in the coating, and their particle size and particulate hardness, and also their aspect ratio, will be selected by a skilled person in accordance with the requirements of the application.

The curable epoxy resin composition of the invention may comprise further additives according to the requirements, examples being defoamers, dispersants, wetting agents, emulsifiers, thickeners, biocides, cosolvents, bases, corrosion inhibitors, flame retardants, release agents and/or waxes.

The curable epoxy resin composition of the invention may also comprise reinforcing fibers such as glass fibers or carbon fibers. These fibers may take the form, for example, of short fiber pieces of a few mm to cm in length, or else continuous fibers, fiber windings or woven fiber fabrics.

The present invention further relates to a process for preparing a cured epoxy resin, comprising the curing of the curable epoxy resin composition.

The curing may take place under atmospheric pressure and at temperatures of less than 250° C., more particularly at temperatures less than 235° C., preferably at temperatures less than 220° C., more particularly in a temperature range from 40° C. to 220° C.

Curing of the curable epoxy resin composition to moldings takes place typically in a mold until dimensional stability has been achieved and the workpiece can be removed from the mold. The subsequent operation for removing inherent stresses in the workpiece and/or for completing the crosslinking of the curable epoxy resin is called heat-conditioning. In principle it is also possible to carry out the heat-conditioning process before the workpiece is removed from the mold, for the purpose of completing the crosslinking, for instance. The heat-conditioning operation typically takes place at temperatures at the limit of dimensional stiffness (Menges et al., "Werkstoffkunde Kunststoffe" (2002), Hanser-Verlag, 5th edition, p. 136). Heat-conditioning takes place typically at temperatures from 120° C. to 220° C., preferably at temperatures from 150° C. to 220° C. The cured workpiece is exposed to the heat-conditioning conditions typically for a time period of 30 to 240 minutes. Longer heat-conditioning times may also be appropriate, depending on the dimensions of the workpiece.

In the curing of the curable epoxy resin composition to form coatings, the substrate to be coated is first of all treated with the curable epoxy resin composition, after which the curable epoxy resin composition on the substrate is cured.

The treatment of the curable epoxy resin composition may take place before or after the shaping of the desired article, by dipping, spraying, roller application, spread application, knife coating, or the like, in the case of liquid formulations, or by application of a powder coating material. Application may take place to individual pieces (e.g., can parts) or to fundamentally continuous substrates, such as to strip rolls of steel in the case of coil coating, for example. Suitable substrates are typically those of steel, tinplate (galvanized steel) or aluminum (for beverage cans, for example). Curing of the curable epoxy resin composition following application to the substrate takes place typically in the temperature range from 20° C. to 250° C., preferably from 50° C. to 220° C., more preferably from 100° C. to 220° C. The time is typically 0.1 to 60 min, preferably 0.5 to 20 min, more preferably 1 to 10 min.

A comprehensive description of the common types of metal packaging and their production, metals and alloys used, and coating techniques is given in P. K. T. Oldring and U. Nehring: Packaging Materials, 7th Metal Packaging for Foodstuffs, ILSI Report, 2007, hereby incorporated by reference.

The present invention further relates to the cured epoxy resins obtained or obtainable by curing the curable epoxy resin composition of the invention, more particularly in the form of coatings on metallic substrates.

The present invention further relates to the use of the compounds of the formula I of the invention and of the curable epoxy resin composition of the invention for producing adhesives, composite materials, moldings, and coatings, more particularly coatings, preferably on containers, more particularly on containers for the storage of food.

The present invention further relates to the use of the compounds of the formula I of the invention as reactive diluents, more particularly as reactive diluents for BADGE- or BFDGE-based epoxy resins. Compounds of the formula I of the invention are suitable for lowering the viscosity of other epoxy resins, especially BADGE- or BFDGE-based epoxy resins, in the resin component and in the curable composition. Advantageously, the addition of the inventive compounds of the formula I as reactive diluents leads to a comparatively small reduction in the glass transition temperature.

The glass transition temperature (Tg) can be determined by means of dynamic mechanical analysis (DMA), for example according to standard DIN EN ISO 6721, or with a differential calorimeter (DSC), for example according to standard DIN 53765. DMA involves subjecting a rectangular test specimen to torsional load at an imposed frequency and with defined deformation. The temperature is raised with a defined ramp, and storage modulus and loss modulus are recorded at fixed time intervals. The former represents the stiffness of a viscoelastic material. The latter is proportional to the work dissipated in the material. The phase displacement between the dynamic stress and the dynamic deformation is characterized by the phase angle δ. The glass transition temperature can be determined by different methods: as the maximum of the tan δ curve, as the maximum of the loss modulus or by means of the tangent method on the storage modulus. In the case of determination of the glass transition temperature using a differential calorimeter, a very small amount of sample (about 10 mg) is heated in an aluminum crucible and the heat flux is measured relative to a reference crucible. This cycle is repeated three times. The glass transition is determined as the mean from the second and third measurements. The evaluation of the Tg level of the heat flux curve can be determined via the turning point, by the half-width, or by the method of the mid-point temperature.

The term "pot life" is understood to mean a parameter which is typically utilized to compare the reactivity of various resin/curing agent or resin/curing agent mixture combinations. The measurement of the pot life is a method for characterization of the reactivity of lamination systems by means of a temperature measurement. According to the application, deviations from the parameters described therein (amount, test conditions and measurement method) have become established. The pot life is determined as follows: 100 g of the curable composition comprising epoxy resin and curing agent or curing agent mixture are charged to a vessel (typically a paper cup). A temperature sensor is immersed into this curable composition and measures and records the temperature at particular time intervals. As soon as this curable composition has solidified, the measurement is ended and the time before attainment of the maximum temperature is found. If the reactivity of a curable composition is too low, this measurement is conducted at elevated temperature. When stating the pot life, the test temperature must always be stated as well.

The gel time (also gelling time), according to DIN 16 945, gives an indication of the period of time between the addition of the curing agent to the reaction mixture and the transition of the reactive resin composition from the liquid state to the gel state. The temperature plays an important role, and therefore the gel time is found in each case for a predetermined temperature. With the aid of dynamic-mechanical methods, especially rotational viscometry, it is possible to examine even small amounts of sample quasi-isothermally and record the entire viscosity or stiffness profile thereof. According to standard ASTM D 4473, the point of intersection between the storage modulus G' and the loss modulus G" where the damping tan δ has the value of 1, is the gel point, and the period of time from addition of the curing agent to the reaction mixture until the attainment of the gel point is the gel time. The gel time thus determined can be regarded as a measure of the curing rate.

The Shore hardness is a characteristic parameter for polymers, for example cured epoxy resins, which is directly related to the penetration depth of an indenter into the test specimen, and is thus a measure for the hardness of the test specimen. It is determined, for example, in accordance with the standard DIN ISO 7619-1. A distinction is made between the Shore A, C and D methods. The indenter used is a spring-loaded pin made from hardened steel. The indenter is pressed into the test specimen with spring force, and the penetration depth represents a measure of the Shore hardness. While the indenter used for the determination of Shore hardnesses A and C is a frustocone having an end face of 0.79 mm in diameter and an opening angle of 35°, the indenter used in the Shore D hardness testing is a frustocone having a conical tip with a radius of 0.1 mm and an opening angle of 30°. For the determination of the Shore hardness characteristics, a scale ranging from 0 Shore (penetration depth 2.5 mm) to 100 Shore (penetration depth 0 mm) has been introduced. The scale value 0 corresponds to the maximum possible impression, meaning that the material offers no resistance to the penetration of the indenter. In contrast, the scale value 100 corresponds to a very high resistance of the material to the penetration, and virtually no impression is produced.

In the determination of the Shore hardness, the temperature plays a crucial role, and so the measurements have to be conducted as per the standard within a restricted temperature interval of 23° C.±2° C.

FIG. 1 shows the viscosity profile of an MPPD DGE epoxy resin and of a BADGE epoxy resin for curing with IPDA at 40° C. (viscosity (y-axis) in mPas against the time (x-axis) in min).

The invention is now illustrated by the following nonlimiting examples.

EXAMPLE 1

Preparation of Monomeric MPPD DGE

2-Methyl-2-phenyl-1,3-propanediol (MPPD; 0.05 mol, 8.31 g) is dissolved in epichlorohydrin (0.4 mol, 37.01 g) and stirred at RT for 30 minutes. Then powdered KOH (0.3 mol, 16.83 g) is added cautiously in portions and the mixture is stirred at RT until conversion is complete. This is followed by addition of 100 ml of water and 30 minutes of stirring at RT. The reaction mixture is extracted repeatedly with methyl tert-butyl ether (MTBE). The combined organic phases are dried over $MgSO_4$, filtered, and concentrated.

The resulting epoxy resin has an epoxide equivalent weight (EEW) of 150-170 g/eq and consists to an extent of approximately 70 weight % of monomeric MPPD DGE (determined semiquantitatively by GPC-MALDI-MS).

The remaining 30 weight % is made up of oligomeric MPPD DGE, consisting to an extent of about 50 weight % of a dimer whose secondary hydroxyl group is likewise glycidylated (overall, a trifunctional compound relative to the epoxide groups). The remainder consists of the dimer not glycidylated on the secondary hydroxyl group, and of MPPD DGE oligomers of higher molecular mass.

The monomeric MPPD DGE can by purified chromatographically to remove the oligomers.

EXAMPLE 1a

Alternative Preparation of Monomeric MPPD DGE 6 mol of MPPD are admixed at 90° C. with 38 mmol of tin(IV) chloride. 12 mol of epichlorohydrin are added in small portions over 3 h, in the course of which the temperature should not fall below 90° C. or rise above 120° C. After cooling to room temperature, 25% sodium hydroxide solution (11 mmol) is added and the mixture is heated to reflux for 2 h. Subsequently, the phases are separated and the product is washed repeatedly with water. The product is obtained in quantitative yield.

The epoxy resin thus obtained has an epoxide equivalent weight (EEW) of 150 to 210 g/eq and consists to an extent of 60 to 90% by weight of monomeric MPPD DGE (determined by NMR). The remaining 10 to 40% comprises dimeric and oligomeric MPPD DGE, which may comprise a portion of organically bound chlorine.

It is also possible to use other Lewis acids in place of tin(IV) chloride, and other bases in place of sodium hydroxide solution.

The monomeric MPPD DGE can be purified to free it of the oligomers by distillation or chromatography.

EXAMPLE 2

Preparation of Oligomeric MPPD DGE 19.5 g of MPPD are dissolved in 40 g of the reaction product from Example 1 (70 weight % monomeric MPPD DGE) in 60 g of methoxypropyl acetate and heated at 140° C. for about 3 d, with successive addition of 2.5 g of catalyst (Anchor 10-40, from Air Products) until the desired EEW has been reached.

EXAMPLE 2a

Alternative Preparation of Oligomeric MPPD DGE 19.5 g of MPPD together with 40 g of the reaction product from example 1a are dissolved in 60 g of methoxypropyl acetate, and a 5-50% solution of 2.5 g of catalyst (Anchor 1040, from Air Products) in methoxypropyl acetate is added dropwise at 140° C. After the addition has ended, the reaction solution is stirred until the desired EEW has been attained.

EXAMPLE 3

Preparation of Cured Epoxy Resin from Monomeric MPPD DGE

MPPD DGE from example 1 (70 weight % monomeric MPPD DGE, EEW 155 g/eq) was mixed, immediately after preparation and without further purification, with a stoichiometric amount of an aminic curing agent. Curing agents used were IPDA, TETA or polyetheramine D230. For comparison, corresponding stoichiometric mixtures of bisphenol A based epoxy resin (BADGE; Epilox A19-03 from Leuna Harze, EEW 182 g/eq) and the aminic curing agents were prepared. The mixtures were incubated at 23° C., 40° C. or 75° C.

At the different temperatures, the rheological measurements for investigating the reactivity profile were carried out on a shear rate-controlled plate/plate rheometer (MCR 301 from Anton Paar) having a plate diameter of 15 mm and a slot distance of 0.25 mm.

The measurement of the gel time was carried out on the abovementioned rheometer in rotational oscillation at 23° C. and 75° C. The point of intersection of loss modulus (G") and storage modulus (G') yields the gel time. The average start viscosity during 2 to 5 minutes following preparation of the mixture was measured at 23° C., 40° C., and 75° C. The results of the measurements are compiled in tables 1 to 5.

For curing with a stoichiometric amount of IPDA at 40° C., the viscosity profile is shown in FIG. 1.

The glass transition temperature (Tg) was measured by means of DSC analysis (Differential Scanning Calorimetry)

of the curing reaction in accordance with ASTM D 3418 on the second run. The temperature profile operated for the measurement was as follows: 0° C.→5 K/min 180° C.→30 min 180° C.→20 K/min 0° C.→20 K/min 220° C. The results of these Tg measurements are compiled in tables 6 and 7.

TABLE 1

Gel times (in min) at 23° C.

|  | IPDA | TETA |
|---|---|---|
| BADGE (EEW 182 g/eq) | 451 | 325 |
| MPPD DGE (EEW 155 g/eq) | 2019 | 551 |

TABLE 2

Start viscosity (in mPas) at 23° C.

|  | IPDA | TETA |
|---|---|---|
| BADGE (EEW 182 g/eq) | 2629 | 2900 |
| MPPD DGE (EEW 155 g/eq) | 14 | 13 |

TABLE 3

Gel times (in min) at 75° C.

|  | IPDA | TETA | D230 |
|---|---|---|---|
| BADGE (EEW 182 g/eq) | 39 | 18 | 60 |
| MPPD DGE (EEW 155 g/eq) | 61 | 12 | 99 |

TABLE 4

Start viscosity (in mPas) at 75° C.

|  | IPDA | TETA | D230 |
|---|---|---|---|
| BADGE (EEW 182 g/eq) | 93 | 106 | 39 |
| MPPD DGE (EEW 155 g/eq) | 17 | 17 | 13 |

TABLE 5

Start viscosity (in mPas) at 40° C.

|  | IPDA |
|---|---|
| BADGE (EEW 182 g/eq) | 426 |
| MPPD DGE (EEW 155 g/eq) | 15 |

TABLE 6

Glass transition temperature (in ° C.) for the composition in the second run of the DSC analysis, without prior curing

| Resin used | IPDA | TETA | D230 |
|---|---|---|---|
| BPA-based (EEW 182 g/eq) | 159 | 143 | 93 |
| MPPD-based (EEW 155 g/eq) | 73 | 59 | 30 |

TABLE 7

Glass transition temperature (in ° C.) for the composition in the second run of the DSC analysis after curing (at 1 K/min to 180° C. and subsequently 30 minutes at 180° C.)

| Resin used | IPDA | TETA | D230 |
|---|---|---|---|
| BPA-based (EEW 182 g/eq) | 169 | 137 | 96 |
| MPPD-based (EEW 155 g/eq) | 86 | 56 | 39 |

The measurements show that with the MPPD DGE based resin a much lower glass transition temperature is achieved, which suggests an increased flexibility. Furthermore, a significantly lowered start viscosity and also a reduced reactivity are found in the case of curing with customary amino hardeners.

EXAMPLE 4

Production of Coatings from Cured Epoxy Resin Based on Oligomeric MPPD DGE

Oligomeric MPPD DGE from example 2 was used without further work-up as the epoxy resin for producing coatings from cured epoxy resin on galvanized steel plate. For comparison, bisphenol A-based epoxy resin (Beckopox EP 307, EEW: 1400 to 1900 g/eq; from Cytec Industries Inc.) was used. First of all, 50% strength solutions of the epoxy resins in methoxypropyl acetate (MPA) were prepared. The epoxy resin solutions were then mixed with a phenolic resin (Phenodur PR 516/60B from Cytec Industries Inc.) as curing agent and with a phosphoric acid-based catalyst (Cycat XK 406 N from Cytec Industries Inc.) and also with further MPA. The proportions of the mixtures (amounts in weight % based on the overall mixture) are compiled in table 8. The mixtures were then applied by knife coating using a knife drawing apparatus (Graf, MTV Messtechnik OHG, 20 μm wire doctor, 80 mm/s drawing speed) onto the previously degreased substrate (E 2.8/2.8, a tinplate coated on both sides with 2.8 g of tin per m$^2$, as commonly used for the production of cans for foodstuffs).

The coatings were baked at 200° C. for 12 minutes. A dry film thickness of 5 to 6 μm was established. Baking on the galvanized steel sheet produced a golden yellow coloration of the coating, of the kind customary for interior can coatings (gold varnish).

TABLE 8

Compositions of the epoxy resin mixtures for coating experiments

| Component | Comparative | Batch 1 | Batch 2 | Function |
|---|---|---|---|---|
| Beckopox EP 307, 50% in MPA | 51.23 |  |  | Bisphenol A based epoxy resin |
| Oligomeric MPPD DGE as per example 2, 50% in MPA |  | 57.95 | 55.0 | Epoxy resin |
| Phenodur PR 516/60B | 18.28 | 11.57 | 14.60 | Curing agent (phenolic resin) |
| Cycat XK 406 N | 1.1 | 1.1 | 2.1 | Phosphoric acid based catalyst |
| MPA | 29.39 | 29.38 | 28.30 | Solvent |

EXAMPLE 5

Testing of Coatings of Cured Epoxy Resin Based on Oligomeric MPPD DGE

The adhesion of the coatings from example 4 to the unpretreated galvanized steel sheet was carried out by means of a cross-cut test in accordance with DIN EN ISO 2409. The cross-cuts in the relatively thin and transparent coatings were very hard to assess with the naked eye, and so microscope pictures at 10 times magnification were prepared. All of the coatings gave the best score of GT 0.

The flexibility of the coatings from example 4 was tested by means of Erichsen impact testing in accordance with DIN EN ISO 6272 and DIN EN 13523-5 (impact tester model 304). Tests with ball drop heights of 20, 50, 70 and 100 cm were conducted. None of the coatings showed cracks (at any of the drop heights). The substrate was dented in the test.

To test the resistance toward acidic media, a practical test with commercial soda containing citric acid was carried out. For this test, the cured coatings from example 4 were wetted with a constant volume of the citric acid soda, and the area of wetting was covered with a watch glass. After exposure times of 5 hours and 24 hours, the wetted areas were inspected. In no case was there damage (edges, blistering, discoloration, or detachment) to the coating.

EXAMPLE 6

Use of Monomeric MPPD DGE as a Reactive Diluent

Bisphenol A-based epoxy resin (BADGE; Epilox A19-03 from LEUNA Harze, EEW 182 g/eq) was mixed with 10% by weight of the MPPD DGE from example 1a (to about 70+/− 10% by weight of monomeric MPPD DGE (determined by NMR), EEW 187 g/eq, immediately after the preparation and without further purification) as a reactive diluent. This resin mixture was admixed with a stoichiometric amount of the aminic curing agent MXDA (m-xylenediamine, Sigma-Aldrich).

For comparison, corresponding resin mixtures without reactive diluent or with 10% by weight of hexanediol diglycidyl ether (HDDGE) (Epilox P13-20 LEUNA Harze) or C12-C14 monoglycidyl ether (C12-C14-MGE) (Epilox P13-18, LEUNA Harze) as reactive diluents were prepared and likewise admixed with the appropriate stoichiometric amount of the aminic curing agent MXDA. The mixtures were incubated at 10° C., 23° C. or 75° C.

The rheological measurements were conducted according to example 3.

The measurement of the gel time was conducted according to example 3 at 10° C., 23° C. and 75° C. The mean start viscosity over 2 to 5 min after production of the mixture was measured at 23° C. The results of the measurements are compiled in tables 9 and 10.

TABLE 9

Gel times (in min) at 10° C., 23° C. and 75° C.

|  | 10° C. | 23° C. | 75° C. |
|---|---|---|---|
| BADGE | 1011 | 383 | 19.5 |
| BADGE + HDDGE | 1165 | 462 | 18.0 |
| BADGE + C12-C14-MGE | 1446 | 565 | 21.0 |
| BADGE + MPPD-DGE | 471 | 416 | 17.5 |

TABLE 10

Start viscosity (in mPas) at 23° C.

| BADGE | 12000 |
|---|---|
| BADGE + HDDGE | 3253 |

TABLE 10-continued

Start viscosity (in mPas) at 23° C.

| BADGE + C12-C14-MGE | 2123 |
|---|---|
| BADGE + MPPD-DGE | 7600 |

To determine the pot life, 100 g of the respective reactive resin composition composed of resin mixture and was stirred up in a paper cup, provided with a temperature sensor and stored at 23° C. The temperature of the sample is recorded as a function of time. The time within which the sample has attained the maximum temperature is the pot life. In addition, the time before attainment of 50° C. is determined. The results of the measurements are compiled in table 11.

TABLE 11

Pot life ($t_o$) at 23° C., and maximum temperature ($T_{max}$) and time before attainment of 50° C. ($t_{50}$)

|  | $t_o$ (in min) | $T_{max}$ (in ° C.) | $t_{50}$ (in min) |
|---|---|---|---|
| BADGE | 118 | 243 | 108 |
| BADGE + HDDGE | 104 | 234 | 93 |
| BADGE + MPPD DGE | 102 | 238 | 93 |

The glass transition temperature is measured as described in example 3. The results of the measurements are compiled in table 12.

TABLE 12

Glass transition temperature (in ° C.)

| BADGE | 126.6 |
|---|---|
| BADGE + HDDGE | 96.7 |
| BADGE + C12-C14 MGE | 100.9 |
| BADGE + MPPD DGE | 115.6 |

To examine the mechanical properties of the corresponding thermosets, the respective reactive resin compositions composed of resin mixture and curing agents are mixed in a Speedmixer (1 min at 2000 rpm), degassed by applying reduced pressure (1 mbar) at 23° C., and then cured to moldings (2 h at 80° C., 3 h at 125° C.). The mechanical tests are conducted to ISO 527-2:1993 and ISO 178:2006. In addition, the Shore D hardness of the thermosets thus cured is determined on the corresponding moldings (thickness 3 mm) at 23° C. by means of a durometer (TI Shore test bench, Sauter Messtechnik). The results of the measurements are compiled in table 13.

TABLE 13

Mechanical data for the cured reactive resin compositions

|  | BADGE | BADGE + HDDGE | BADGE + C12-C14 MGE | BADGE + MPPD DGE |
|---|---|---|---|---|
| Tensile strength (in MPa) | 71.2 | 77.1 | 68.1 | 72.2 |
| Tensile elongation (in %) | 5.55 | 3.58 | 5.31 | 6.42 |
| Tensile modulus E (in MPa) | 2894 | 3549 | 3033 | 3074 |
| Flexural strength (in MPa) | 110 | 135 | 111 | 113 |
| Flexural elongation (in %) | 6.1 | 5.42 | 6.09 | 6.1 |

TABLE 13-continued

Mechanical data for the cured reactive resin compositions

|  | BADGE | BADGE + HDDGE | BADGE + C12-C14 MGE | BADGE + MPPD DGE |
|---|---|---|---|---|
| Flexural modulus (in MPa) | 3030 | 3618 | 3104 | 3151 |
| Shore D hardness | 91 | 86 | 88 | 90 |

The lowering of the glass transition temperature which generally accompanies the addition of reactive diluents is comparatively small in the case of use of MPPD DGE as the reactive diluent. Compared to HDDGE, where a certain degree of embrittlement (lowering of the tensile and flexural elongation) is observed on addition thereof, the mechanical data are altered only slightly compared to the pure resin by the addition of MPPD DGE.

COMPARATIVE EXAMPLE 1

Preparation of 2-phenyl-1,2-propanediol diglycidyl ether (1,2-PD DGE) and Curing Thereof 2-Phenyl-1,2-propanediol (1,2-PD) is reacted in accordance with example 1 with epichlorohydrin to give the diglycidyl ether (1,2-PD DGE with EEW of 192 g/eq), and then, without further purification, cured with IPDA in a stoichiometric mixture according to example 3. Gel time and start viscosity at 23° C. and 75° C. and glass transition temperature were determined according to example 3. The results of the measurements are compiled in table 14.

TABLE 14

Gel time and start viscosity for the curing of 1,2-PD DGE with IPDA at 23° C. and 75° C., and glass transition temperature for the composition in the 2nd run in the DSC analysis without prior curing

| Gel time (in min) at 23° C. | 2928 |
| Gel time (in min) at 75° C. | 53 |
| Start viscosity (in mPas) at 23° C. | 240 |
| Start viscosity (in mPas) at 75° C. | 23 |
| Glass transition temperature | 56 |

MPPD DGE is preparable in a good yield and can be used even without further purification for the curing. The curing of correspondingly prepared 1,2-PD DGE leads, in contrast, to cured epoxy resin compositions with a distinctly lower glass transition temperature.

The invention claimed is:

1. A diglycidyl ether of a 2-phenyl-1,3-propanediol derivative of formula I:

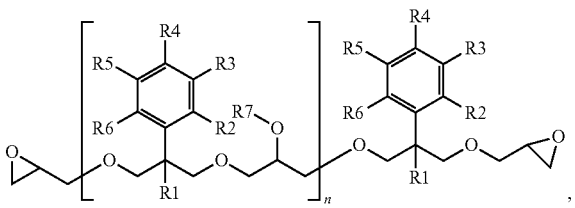

which is derived from a 2-phenyl-1,3-propanediol derivative of formula II:

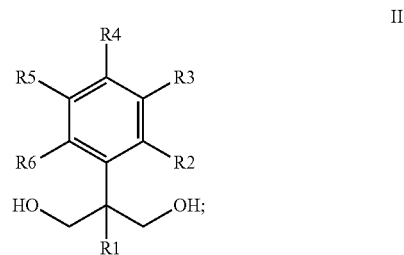

where:
R1 is an alkyl group or an aryl group,
R2 and R3 or R3 and R4 optionally form a fused aromatic ring or a fused heteroaromatic ring, where R2 to R4 are otherwise each independently a hydrogen atom, an alkyl group having 1 to 4 C atoms, a halogen atom, or a nitro group,
R5 and R6 are each independently a hydrogen atom, an alkyl group having 1 to 4 C atoms, a halogen atom, or a nitro group,
R7 is a hydrogen atom or a glycidyl group, and
n is from 0 to 100.

2. The diglycidyl ether of a 2-phenyl-1,3-propanediol derivative according to claim 1,
where:
R1 is an alkyl group having 1 to 5 C atoms or an aryl group having 6 to 10 C atoms,
R2 to R6 are each independently a hydrogen atom or an alkyl group having 1 to 4 C atoms,
R7 is a hydrogen atom or a glycidyl group, and
n is from 0 to 30.

3. The diglycidyl ether of a 2-phenyl-1,3-propanediol derivative according to claim 2,
where:
R1 is an alkyl group having 1 to 4 C atoms,
R2 to R6 are each a hydrogen atom,
R7 is a hydrogen atom or a glycidyl group, and
n is from 0 to 30.

4. A process for preparing the diglycidyl ether of a 2-phenyl-1,3-propanediol derivative according to claim 1, the process comprising:
reacting the 2-phenyl-1,3-propanediol derivative of formula II with epichlorohydrin.

5. A resin component, comprising:
the glycidyl ether of a 2-phenyl-1,3-propanediol derivative according to claim 1, and
at least one epoxy resin selected from the group consisting of a diglycidyl ether of bisphenol A, a diglycidyl ether of bisphenol F, a diglycidyl ether of ring-hydrogenated bisphenol A, a diglycidyl ether of ring-hydrogenated bisphenol F, tetraglycidylmethylenedianiline, a cresol epoxy resin, a novolac epoxy resin, a triglycidyl-aminophenol, and oligomers thereof.

6. A reactive diluent, comprising the diglycidyl ether of a 2-phenyl-1,3-propanediol derivative according to claim 1.

7. An oligomer prepared by reacting one or more diols with one or more diglycidyl ethers of a 2-phenyl-1,3-propanediol derivative of formula I:

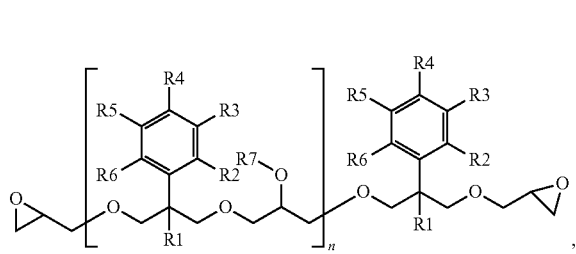

which is derived from a 2-phenyl-1,3-propanediol derivative of formula II:

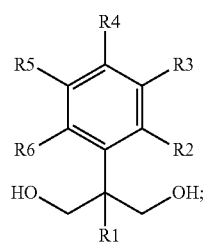

where:

R1 is an alkyl group or an aryl group,

R2 and R3 or R3 and R4 optionally form a fused aromatic ring or a fused heteroaromatic ring, where R2 to R4 are otherwise each independently a hydrogen atom, an alkyl group having 1 to 4 C atoms, a halogen atom, or a nitro group, R5 and R6 are each independently a hydrogen atom, an alkyl group having 1 to 4 C atoms, a halogen atom, or a nitro group, R7 is a hydrogen atom or a glycidyl group, and n is from 0 to 100, provided that n is 0 when one diglycidyl ether of a 2-phenyl-1,3-propanediol derivative is reacted and provided that n is predominantly 0 when two or more diglycidyl ethers of a 2-phenyl-1,3-propanediol derivative having different n values are reacted.

8. A process for preparing the oligomer according to claim 7, the process comprising:

reacting the one or more diols with the one or more diglycidyl ethers of a 2-phenyl-1,3-propanediol derivative of formula I.

9. The oligomer according to claim 7, where the one or more diols are different from the 2-phenyl-1,3-propanediol derivative of formula II.

10. A curable epoxy resin composition, comprising a curing component comprising at least one curing agent, and a resin component comprising at least one compound selected from the group consisting of a diglycidyl ether of a 2-phenyl-1,3-propanediol derivative and an oligomer thereof;

wherein the diglycidyl ether of a 2-phenyl-1,3-propanediol derivative is of formula I:

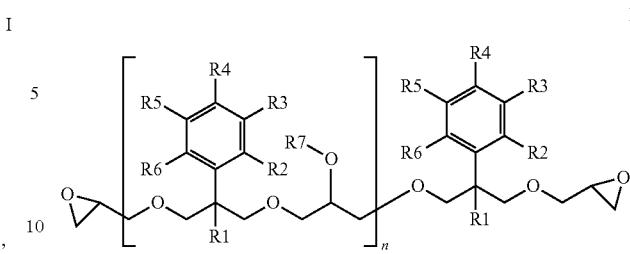

which is derived from a 2-phenyl-1,3-propanediol derivative of formula II:

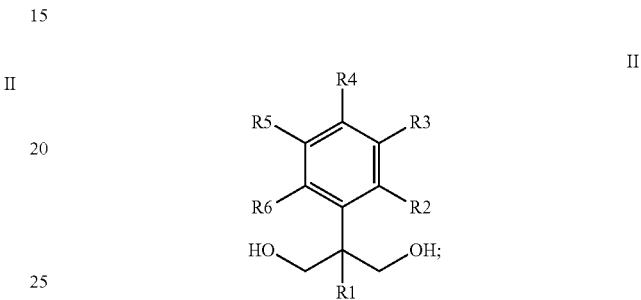

where:

R1 is an alkyl group or an aryl group,

R2 and R3 or R3 and R4 optionally form a fused aromatic ring or a fused heteroaromatic ring, where R2 to R4 are otherwise each independently a hydrogen atom, an alkyl group having 1 to 4 C atoms, a halogen atom, or a nitro group, R5 and R6 are each independently a hydrogen atom, an alkyl group having 1 to 4 C atoms, a halogen atom, or a nitro group, R7 is a hydrogen atom or a glycidyl group, and n is from 0 to 100; and wherein the oligomer is prepared by reacting one or more diols with one or more diglycidyl ethers of a 2-phenyl-1,3-propanediol derivative of formula I, provided that n is 0 when one diglycidyl ether of a 2-phenyl-1,3-propanediol derivative is reacted and provided that n is predominantly 0 when two or more diglycidyl ethers of a 2-phenyl-1,3-propanediol derivative having different n values are reacted.

11. The curable epoxy resin composition according to claim 10, wherein the resin component comprises the diglycidyl ether of a 2-phenyl-1,3-propanediol derivative.

12. The curable epoxy resin composition according to claim 11, wherein the resin component further comprises at least one epoxy resin selected from the group consisting of a diglycidyl ether of bisphenol A, a diglycidyl ether of bisphenol F, a diglycidyl ether of a ring-hydrogenated bisphenol A, a diglycidyl ether of a ring-hydrogenated bisphenol F, tetraglycidylmethylenedianiline, a cresol epoxy resin, a novolac epoxy resin, a triglycidyl-aminophenol, and oligomers thereof.

13. The curable epoxy resin composition according to claim 12, wherein the diglycidyl ether of a 2-phenyl-1,3-propanediol derivative accounts for up to 30% by weight of the resin component.

14. The curable epoxy resin composition according to claim 10, wherein the at least one curing agent is selected from the group consisting of an amino curing agent and a phenolic resin.

15. The curable epoxy resin composition according to claim 10,
wherein the at least one compound selected from the group consisting of a diglycidyl ether of a 2-phenyl-1,3-propanediol derivative and an oligomer thereof accounts for at least 40 weight % of the resin component.

16. The curable epoxy resin composition according to claim 10,
wherein the resin component contains less than 40 weight % of bisphenol A or F based compounds.

17. A method for producing a cured epoxy resin, the method comprising:
curing the curable epoxy resin composition according to claim 10.

18. A cured epoxy resin obtained by the method according to claim 17.

19. A method for producing an adhesive, a composite material, a molding or a coating, the method comprising:
producing an adhesive, a composite material, a molding or a coating with the curable epoxy resin composition according to claim 10.

* * * * *